(12) United States Patent
Bishop et al.

(10) Patent No.: US 11,009,493 B2
(45) Date of Patent: May 18, 2021

(54) HEAT-SEALABLE CHEMICAL VAPOR-SENSOR BAG

(71) Applicant: The United States of America, as represented by the Secretary of the Navy, Crane, IN (US)

(72) Inventors: Michael L. Bishop, Norco, CA (US); Christopher H. Clark, Norco, CA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 249 days.

(21) Appl. No.: 16/262,455

(22) Filed: Jan. 30, 2019

(65) Prior Publication Data

US 2019/0234923 A1 Aug. 1, 2019

Related U.S. Application Data

(60) Provisional application No. 62/623,886, filed on Jan. 30, 2018.

(51) Int. Cl.
*G01N 33/28* (2006.01)
*G01N 33/00* (2006.01)
(Continued)

(52) U.S. Cl.
CPC .......... *G01N 33/0047* (2013.01); *B01L 1/025* (2013.01); *B01L 3/505* (2013.01);
(Continued)

(58) Field of Classification Search
CPC ........... G01N 33/0047; G01N 33/0016; G01N 33/28; B01L 1/025; B01L 3/505; B01L 3/565; B01L 3/567; B01L 2300/048; B01L 2400/06; B01L 2400/0487; B01L 2300/123; B01L 2300/0663; B01L 2300/049

See application file for complete search history.

(56) References Cited

U.S. PATENT DOCUMENTS

| 8,683,672 B2 | 4/2014 | Deshusses et al. |
| 2006/0013744 A1* | 1/2006 | Mikkelsen .............. B32B 27/32 422/400 |

OTHER PUBLICATIONS

Kim, Hyuntae; Konnanath, Bharatan; Sattigeri, Prasanna; et al, "Electronic-nose for detecting environmental pollutants: signal processing and analog front-end design" Published Online Apr. 11, 2011, Analog Integr Circ Sig Process, copyright Springer Sciences+ Business Media, LLC 2011.

* cited by examiner

*Primary Examiner* — Jennifer Wecker
*Assistant Examiner* — Michael Paul Shimek
(74) *Attorney, Agent, or Firm* — Naval Surface Warfare Center, Crane Division; Eric VanWiltenburg

(57) ABSTRACT

The present invention relates to a chemical vapor-sensor bag with an integrated sensor array to verify the presence of specific chemical vapors inside a sealed bag. In an exemplary embodiment, a device can be sealed within a vapor-sensor bag to allow the device to be transported to and tested for contaminants at the point of use by an end user of the device. In another exemplary embodiment, a device can be coupled to a gas port on a vapor-sensor bag to allow gas within the device to be tested for contaminants. In another exemplary embodiment, gas from a device can be streamed through vapor-sensor bag by coupling the device to a first gas port on a vapor-sensor bag and allowing gas to exit the bag through a second gas port.

9 Claims, 6 Drawing Sheets

(51) Int. Cl.
*B01L 1/02* (2006.01)
*B01L 3/00* (2006.01)
(52) U.S. Cl.
CPC ............... *B01L 3/565* (2013.01); *B01L 3/567* (2013.01); *G01N 33/0016* (2013.01); *G01N 33/28* (2013.01); *B01L 2300/048* (2013.01); *B01L 2300/049* (2013.01); *B01L 2300/0663* (2013.01); *B01L 2300/123* (2013.01); *B01L 2400/0487* (2013.01); *B01L 2400/06* (2013.01)

HEAT-SEALABLE CHEMICAL VAPOR-SENSOR BAG

CROSS-REFERENCE TO RELATED APPLICATIONS

This patent application claims the benefit of U.S. Provisional Application No. 62/623,886, titled "HEAT-SEALABLE CHEMICAL VAPOR-SENSOR BAG", filed Jan. 30, 2018, the disclosure of which is expressly incorporated by reference herein.

STATEMENT REGARDING FEDERALLY SPONSORED RESEARCH OR DEVELOPMENT

The invention described herein was made in the performance of official duties by employees of the Department of the Navy and may be manufactured, used and licensed by or for the United States Government for any governmental purpose without payment of any royalties thereon. This invention (Navy Case 200,497) is assigned to the United States Government and is available for licensing for commercial purposes. Licensing and technical inquiries may be directed to the Technology Transfer Office, Naval Surface Warfare Center Corona Division, email: CRNA_CTO@navy.mil.

FIELD OF THE INVENTION

The present invention relates to a chemical vapor-sensor bag with an integrated sensor array to verify the presence of specific chemical vapors inside a sealed bag.

BACKGROUND AND SUMMARY OF THE INVENTION

The present invention relates to a heat-sealable chemical vapor-sensor bag. Hydrocarbon materials are extremely flammable in oxygen-enriched environments and therefore pose a serious safety hazard to personnel if they are allowed to come into contact with oxygen or oxygen-enriched environments. Currently, oxygen pressure gauges and other components that are removed from a parent system for off-site calibration are placed into polyethylene bags which are then heat-sealed for transport to a calibration facility. Upon receipt, the bag is opened and its contents are visually inspected for the presence of hydrocarbon contaminants using visible and ultraviolet (UV) light. Grossly contaminated items are rejected to keep them out of the oxygen cleanroom and to prevent them from coming in contact with calibration equipment. The remaining level of chemical solvent in a solvent-cleaned critical-air or oxygen gauge must be verified to be below stated levels to protect users of these components from breathing unsafe/unhealthy amounts of chemical vapors.

The existing capabilities for measuring the level of solvent vapor remaining in a device under test (e.g., a closed-end Bourdon-tube pressure gauge) require that the cleaned pressure gauge be connected to a source of pressurized clean air or nitrogen and pressurizing the gauge to the lesser of 100 psig or the maximum pressure limit of the gauge. After the gauge is held at pressure for a prescribed length of time, the gas in the gauge must be accurately sampled and measured to obtain a true verification of remaining solvent vapors. Laboratories are attempting to sample the gas as it is expelled from a gauge using a flow-through monitoring instrument, but this dilutes the gas in the gauge with atmospheric air from their laboratory. Furthermore, the types of instruments they are using require a constant flow of gas at a relatively high rate, such that the gas from a typical pressure gauge passes through their instrument in seconds or less and the instrument does not give them an accurate measurement of remaining solvent vapor.

According to an illustrative embodiment of the present disclosure, a heat-sealable bag is used to seal a device for transport and verification of cleanness prior immediately prior to usage. Exemplary bags comprise chemical resistant materials (e.g., polyvinyl fluoride) based on the expected contaminants within the bags. The bags have at least one sensor array integrated into the bag such that gas inside the bag will contact an interior surface of the sensor array. An exterior surface of the sensor array can display a reading (e.g., a binary yes/no reading) indicating whether a contaminant has been detected. Sealing a device in the bag allows an end user of the device to know immediately prior to use whether or not the device is free from contaminants.

According to a further illustrative embodiment of the present disclosure, a heat-sealable bag can include two gas ports, each connecting the interior and exterior of the bag. Each gas port can include a valve to allow or prevent gas flow through the gas port. Closing both valves allows a bag to operate as if there were no gas ports.

Additional features and advantages of the present invention will become apparent to those skilled in the art upon consideration of the following detailed description of the illustrative embodiment exemplifying the best mode of carrying out the invention as presently perceived.

BRIEF DESCRIPTION OF THE DRAWINGS

The detailed description of the drawings particularly refers to the accompanying figures in which.

DETAILED DESCRIPTION OF THE DRAWINGS

The embodiments of the invention described herein are not intended to be exhaustive or to limit the invention to precise forms disclosed. Rather, the embodiments selected for description have been chosen to enable one skilled in the art to practice the invention.

Figure 1:
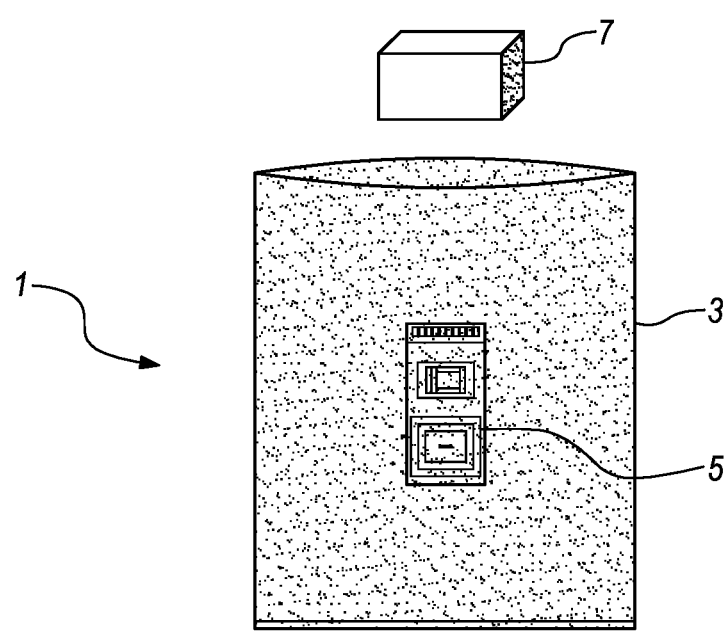
FIG. 1 shows an exemplary vapor-sensor bag and a device under test.

FIG. 1 shows an exemplary vapor-sensor bag 1 to encapsulate a test instrument such as a pressure gauge and to measure chemical vapors within a sealing compartment 3 while the sensor bag 1 remains sealed. The sensor bag 1 is heat-sealable to provide a level of protection against external contaminants. A sensor array 5 and the sealing compartment 3 are conjoined to permit the measurement of chemical vapor concentrations within the sealed sensor bag 1 without opening the bag. The sensor array 5 may measure a concentration of a single chemical vapor such as a solvent or it may approximate a measurement of a class of chemicals such as hydrocarbons, or it may measure a combination different single chemical vapors and/or classes of chemical vapors. In at least some embodiments, sensor array 5 can include a plurality of sensors.

Sensors can be tailored to measure specific chemical compounds. This capability enables the application of the sensor bag 1 to different situations such as measuring residual solvent vapors or measuring the vapor pressure from small amounts of hydrocarbon contaminants. The sensors have capability of measuring to low ppb concentration levels. This capability could provide assurance that the equipment they are using is safe from solvent vapor contamination. It could also provide the justification to eliminate a second solvent rinse in oxygen-cleaning applications, thus providing a significant cost savings. A bag with an integral chemical vapor sensor can provide an accurate measurement of solvent vapor concentration level from a small amount of a gas sample (such as the gas expelled from a pressurized dead-end pressure gauge). The integral sensor eliminates the need for further transfers of sample gas, thus reducing the possibility of contaminating or diluting a gas sample. Each sensor on a vapor-sensor bag 1 can be designed to measure different chemical vapors, combinations of different chemical vapors, or different combinations of different chemical vapors. The sensor array 5 can include a variety of sensors to measure multiple types of vapors or a single sensor to measure a specific type of vapor.

For example, a sensor bag 1 with an integral chemical vapor sensor array 5 can provide a quantitative measurement of hydrocarbon vapor concentration level from a small amount of a hydrocarbon-based oil or grease. The integral sensors can provide this information without opening the bag, thus reducing the risk of introducing hydrocarbon contaminates into cleanrooms or clean areas within a laboratory. It can also replace or supplement a subjective visual inspection with an objective, quantitative measurement. The vapor sensors can have the capability to measure a vapor concentration inside a bag and the capability to communicate with an external device by either wireless or directly-wired means. This embodiment does not require operators to be highly skilled in the operation of chemical measurement instruments. Sensors of this type can be produced at a cost low enough to be considered disposable, as can sealing compartment 3. Vapor sensor bags 1 can also be produced at low cost so that they can be used for one-time applications, such as for transporting oxygen or critical air instruments.

One exemplary embodiment of a vapor-sensor bag 1 is to provide a means to quantitatively verify the presence of off-gassing hydrocarbon contaminant materials on or in an item such as a pressure gauge that is sealed inside a bag and communicate (e.g., through an RF chip) this information to a separate device outside the bag such as a smart phone. Another exemplary embodiment of the vapor-sensor bag 1 is to provide a means to quantitatively verify the presence of chemical solvent vapors on or in an item such as a pressure gauge that is sealed inside a bag and display a visual indicator that a contaminant is present. Placing a device into a sensor bag 1 after visual inspection can allow the device to transported in a controlled environment and allow an end user to independently verify that there are no contaminants in the device immediately prior to use.

Figure 2:
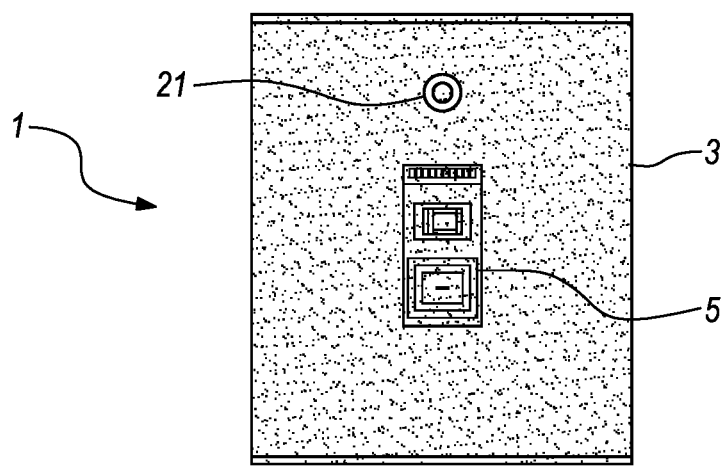
FIG. 2 shows an exemplary vapor-sensor bag with one gas port.

FIG. 2 shows an exemplary vapor-sensor bag 1 to sample gas introduced into a bag from an external item, device, or facility. Vapor-sensor bag 1 is heat sealed prior to use and is drained of any remaining gases inside such that the interior of sensor bag 1 is a vacuum. Sensor array 5 is integrated into the body of sealing compartment 3. A first gas port 21 provides an interface between the interior and exterior of sensor bag 1. First gas port 21 can include a valve which allows the flow of gas between the interior and exterior to be controlled. First gas port 21 provides a means to connect the sensor bag to an instrument (e.g., a closed-end Bourdon-tube pressure gauge) to capture the pressurized gas within such a instrument without risk of contamination or dilution from the operating environment. One exemplary embodiment of a vapor-sensor bag 1 in this configuration is to provide a means to measure the presence of solvent vapors in an external item such as a bourdon-tube pressure gauge and communicate this information to a separate device outside the bag such as a smart phone. Another exemplary embodiment of this configuration is to measure a chemical vapor or multiple chemical vapors in the atmosphere in a room or in a compartment and communicate this information to a separate device outside the bag such as a smart phone.

Figure 3:
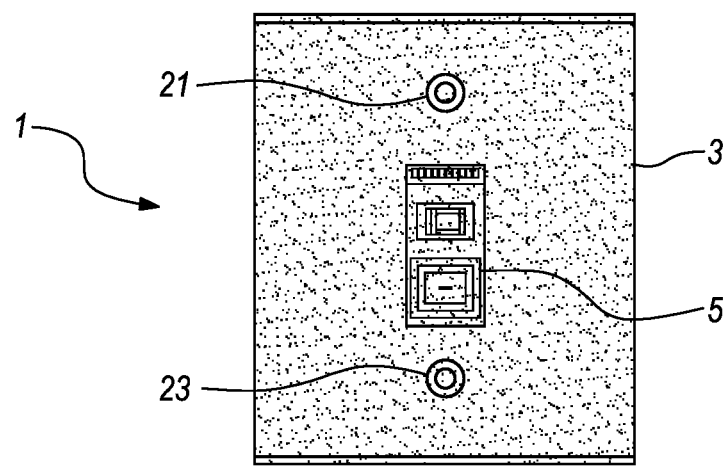
FIG. 3 shows an exemplary vapor-sensor bag with two gas ports.

FIG. 3 shows an exemplary vapor-sensor bag 1 to sample a stream of gas introduced into a bag from a gas source (e.g., an external item, device, or facility). Though the sensor does not require a constant flow of gas, a vapor sensor bag 1 with two gas sampling ports 21, 23 may be used to accurately measure solvent vapor concentration in a flowing gas stream, even when the flow rate is very low. A sensor array 5 should be placed between the first and second gas ports 21, 23 to allow for more accurate sensor readings. In an exemplary usage, a first gas port 21 is connected to a gas source (e.g., a device having a gas reservoir) and a second gas port 23 acts as an exhaust port or is connected to an exhaust outlet (e.g., a tube). Gas can be pumped through the bag by a pump within the gas source or within the exhaust outlet. The gas ports 21, 23 can each have a valve to prevent gas flow through their respective gas ports. Embodiments with gas ports 21, 23 having valves can act as the zero and one gas port embodiments shown in FIGS. 1 and 2, respectively, by closing both or one of the gas port valves.

Another exemplary embodiment of a vapor-sensor bag is to provide a means to quantitatively verify the presence of off-gassing hydrocarbon contaminant materials on or in an item such as a pressure gauge that is sealed inside a bag and communicate this information to a separate device outside the bag such as a smart phone.

Another exemplary embodiment of a vapor-sensor bag is to provide a means to quantitatively verify the presence of chemical solvent vapors on or in an item such as a pressure gauge that is sealed inside a bag and communicate this information to a separate device outside the bag such as a smart phone.

Another exemplary embodiment of a vapor-sensor bag is to provide a means to quantitatively and simultaneously verify the presence of different chemical solvent vapors on or in an item such as a pressure gauge that is sealed inside a bag and communicate this information to a separate device outside the bag such as a smart phone.

Another exemplary embodiment of a vapor-sensor bag is to provide a means to quantitatively and simultaneously verify the presence of different chemical solvent vapors in an external item, device, compartment or room by drawing a sample of gas from the item device, compartment or room into a bag.

Multiple embodiments can be combined (e.g., combining the embodiments shown in FIGS. 1 and 2). For example, a device can be coupled to a first sensor bag, such as that shown in FIG. 2, to fill the first sensor bag with a gas. The first sensor bag and device can then be placed and sealed within a second sensor bag, such as that shown in FIG. 1, for transportation. When an end user receives the second sensor bag, a second sensor array on the second sensor bag can provide a preliminary reading of contaminants within the second sensor bag (e.g., from the exterior of the device). After opening the second sensor bag, a first sensor array on the first sensor bag can provide a secondary reading of contaminants within the first sensor bag (e.g., from within the device).

Figure 4:
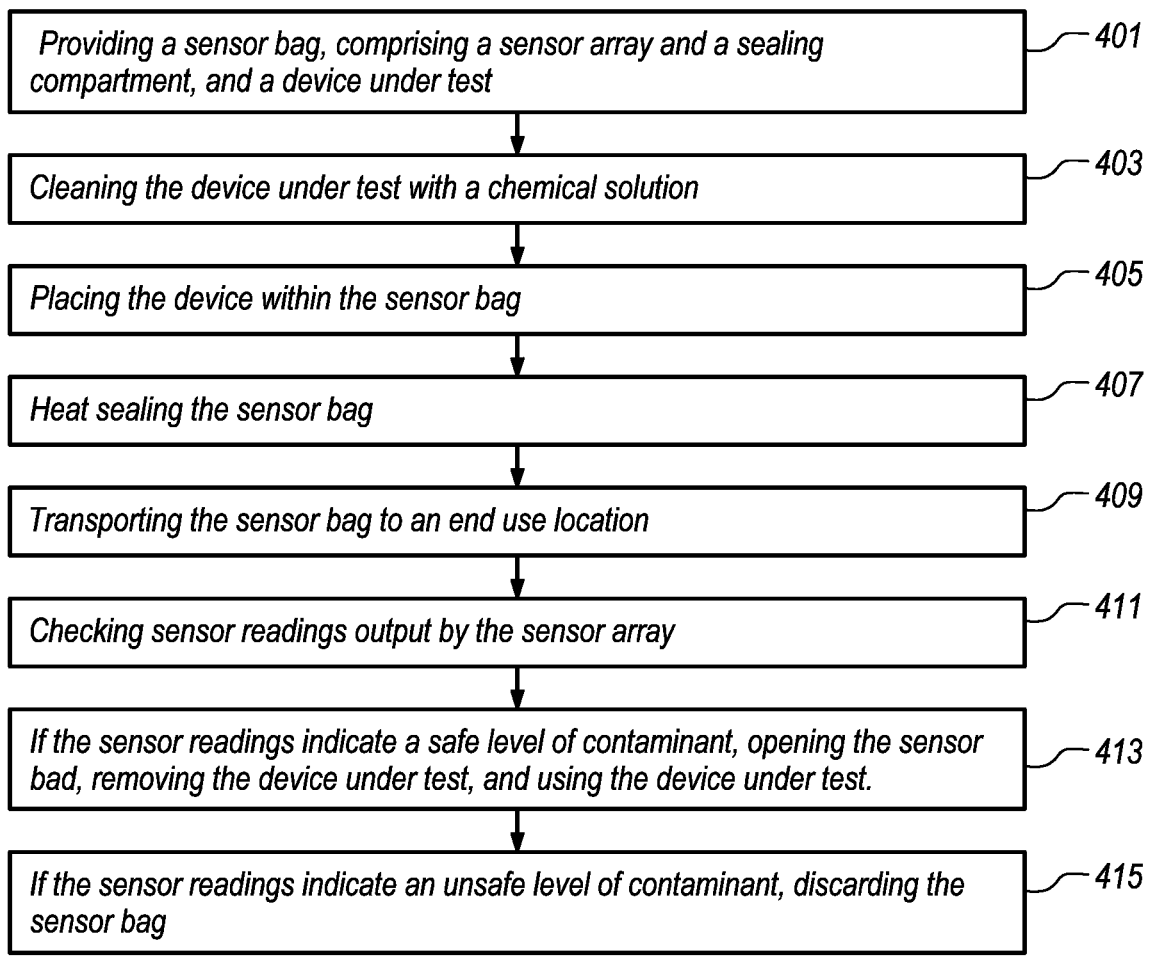
FIG. 4 shows an exemplary method of sealing a device within a vapor-sensor bag.

FIG. 4 shows an exemplary method of sealing a device within a vapor-sensor bag to test for contaminants. At step 401: Providing a sensor bag, comprising a sensor array and a sealing compartment, and a device under test. At step 403: Cleaning the device under test with a chemical solution (e.g., CFC-113). At step 405: Placing the device within the sensor bag. At step 407: Heat sealing the sensor bag. At step 409: Transporting the sensor bag to an end use location. At step 411: Checking sensor readings output by the sensor array. At step 413: If the sensor readings indicate a safe level of contaminant, opening the sensor bag, removing the device under test, and using the device under test. At step 415: If the sensor readings indicate an unsafe level of contaminant, discarding (e.g., throwing away, transporting to a cleaning facility, etc.) the sensor bag. Optionally, between steps 405 and 407, step 406: draining environmental gas from the sensor bag and pumping a first gas composition (e.g., nitrogen) into the sensor bag. Step 406 can be controlled to allow a predetermined pressure to be maintained within the sensor bag during transport.

Figure 5:
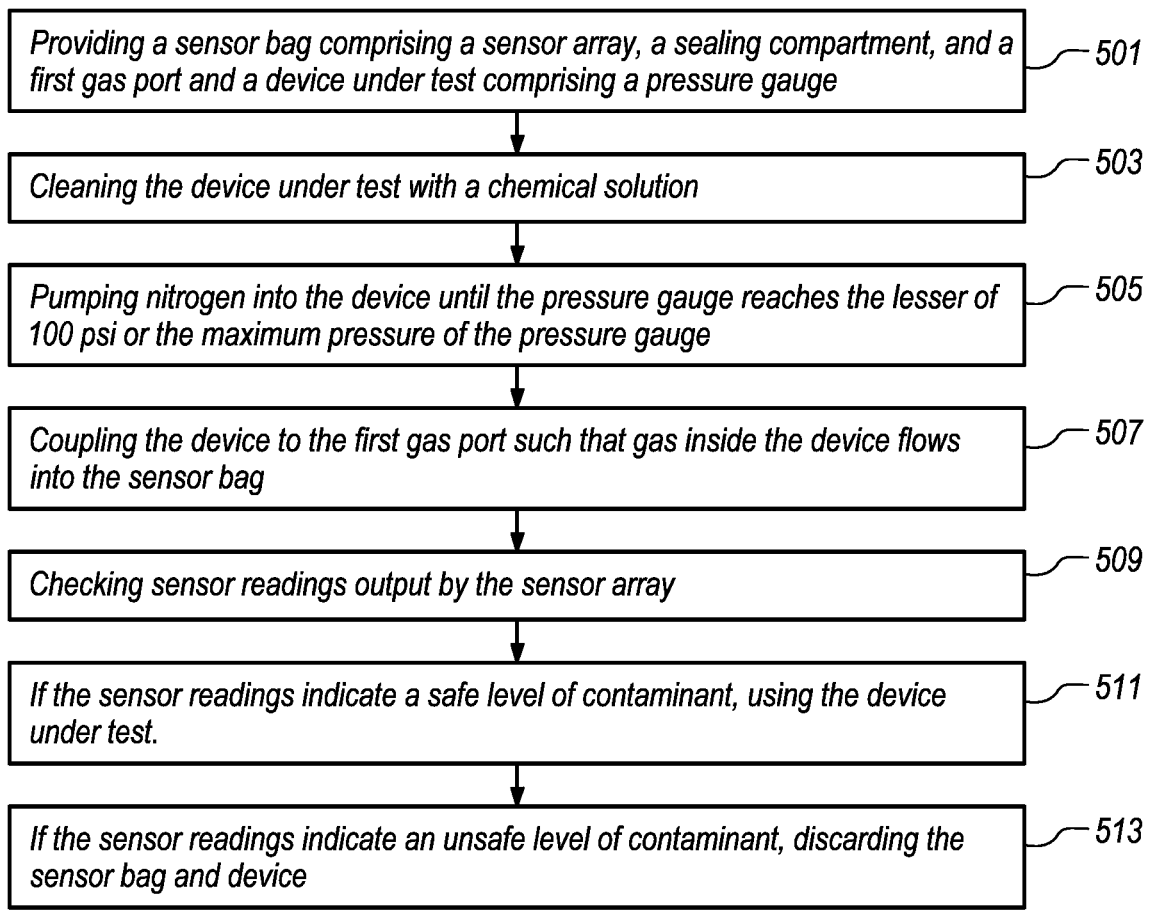
FIG. 5 shows an exemplary method of testing a device by coupling the device to a sensor bag.

FIG. 5 shows an exemplary method for testing a device by coupling the device to a sensor bag. Step 501: Providing a sensor bag comprising a sensor array, a sealing compartment, and a first gas port and a device under test comprising a pressure gauge. At step 503: Cleaning the device under test with a chemical solution. At step 505: Pumping nitrogen into the device until the pressure gauge reaches the lesser of 100 psi or the maximum pressure of the pressure gauge. At step 507: Coupling the device to the first gas port such that gas inside the device flows into the sensor bag. At step 509: Checking sensor readings output by the sensor array. At step 511: If the sensor readings indicate a safe level of contaminant, using the device under test. At step 513: If the sensor readings indicate an unsafe level of contaminant, discarding the sensor bag and device.

Figure 6:
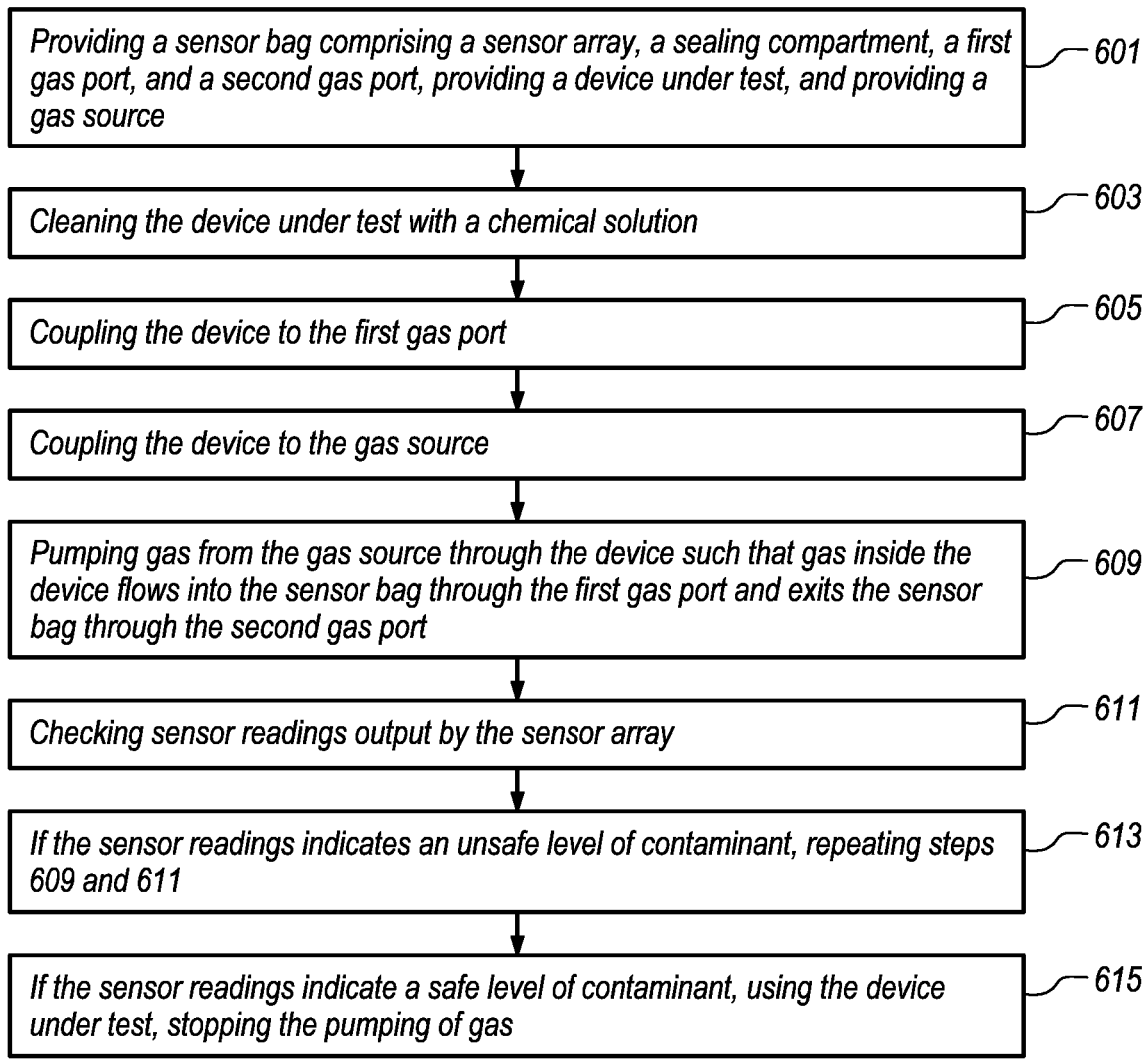
FIG. 6 shows an exemplary method of testing a device by coupling the device to a sensor bag and gas source.

FIG. 6 shows an exemplary method for testing a device by coupling the device to a sensor bag and gas source. Step 601: Providing a sensor bag comprising a sensor array, a sealing compartment, a first gas port, and a second gas port, providing a device under test, and providing a gas source. At step 603: Cleaning the device under test with a chemical solution. At step 605: Coupling the device to the first gas port. At step 607: Coupling the device to the gas source. At step 609: Pumping gas from the gas source through the device such that gas inside the device flows into the sensor bag through the first gas port and exits the sensor bag through the second gas port. At step 611: Checking sensor readings output by the sensor array. At step 613: If the sensor readings indicate an unsafe level of contaminant, repeating steps 609 and 611. At step 615: If the sensor readings indicate a safe level of contaminant, using the device under test, stopping the pumping of gas.

Although the invention has been described in detail with reference to certain preferred embodiments, variations and modifications exist within the spirit and scope of the invention as described and defined in the following claims.

The invention claimed is:

1. A vapor-sensor bag comprising:
   a sealing compartment;
   a sensor array integrated within the sealing compartment such that a first side of the sensor array faces an interior of the sealing compartment and a second side of the sensor array faces an exterior of the sealing compartment,
   a device, encapsulated inside the sealing compartment, and configured to measure chemical vapors within a sealing compartment while the sensor bag remains sealed,
   wherein the sensor array comprises at least one sensor, wherein each sensor of the at least one sensor is configured to detect at least one chemical or chemical mixture without opening the sensor bag;
   at least two gas ports, wherein each gas port comprises a valve, wherein each valve of each gas port has an open state permitting the flow of gas through the gas port and a closed state blocking the flow of gas through the gas port.

2. The vapor-sensor bag of claim 1, wherein the sealing compartment comprises polyvinyl fluoride and the at least one chemical or chemical mixture is CFC-113.

3. A method of testing a device for chemicals comprising:
   providing a vapor-sensor bag, wherein the vapor-sensor bag comprises a sensor array, a sealing compartment, and a first gas port and a device under test;
   cleaning the device by passing a cleaning chemical solution through the device;
   placing the device within the vapor-sensor bag;
   heat-sealing the vapor-sensor bag;
   and the sensor array detecting at least one chemical cleaning composition remaining in the device, therefore indicating contamination while the sensor bag remains sealed.

4. The method of claim 3, further comprising after the heat-sealing step:
   transporting the vapor-sensor bag to an end use location;
   checking the chemical detection output;
   if the chemical detection output indicates a safe amount of the first chemical composition within the device, opening the vapor-sensor bag, removing the device, and using the device; and
   if the contaminant detection output indicates an unsafe amount of the first chemical composition within the device, discarding the vapor-sensor bag.

5. The method of claim 3, wherein the vapor-sensor bag comprises:
   a sealing compartment;
   a sensor array integrated with the sealing compartment such that a first side of the sensor array faces an interior of the sealing compartment and a second side of the sensor array faces an exterior of the sealing compartment, wherein the sensor array comprises at least one sensor, wherein each sensor of the at least one sensor is configured to detect at least one chemical or chemical mixture; and
   at least two gas ports, wherein each gas port comprises a valve, wherein each valve of each gas port has an open state permitting the flow of gas through the gas port and a closed state blocking the flow of gas through the gas port;
   wherein the sensor array performs the generating step by generating at least one signal when a predetermined chemical;
   wherein the at least one chemical or chemical mixture comprises the first chemical composition.

6. A method of testing a device for chemicals comprising:
   providing a vapor-sensor bag and the device, wherein the vapor-sensor bag comprises a first gas port;

passing a chemical solution comprising a first chemical composition through the device;

pressurizing the device with a first gas composition such that the first gas composition mixes with remaining portions of the chemical solution within the device to create a first gas mixture;

coupling the device to the first gas port with the first gas port in a closed state;

opening the first gas port to allow the first gas mixture to pass into the vapor-sensor bag;

generating at least one chemical detection output;

if the chemical detection output indicates a safe amount of the first chemical composition within the device, using the device; and if the contaminant detection output indicates an unsafe amount of the first chemical composition within the device, discarding the vapor-sensor bag and device.

7. The method of claim 6, wherein the vapor-sensor bag comprises:

a sealing compartment;

a sensor array integrated with the sealing compartment such that a first side of the sensor array faces an interior of the sealing compartment and a second side of the sensor array faces an exterior of the sealing compartment, wherein the sensor array comprises at least one sensor, wherein each sensor of the at least one sensor is configured to detect at least one chemical or chemical mixture; and at least two gas ports, wherein each gas port comprises a valve, wherein each valve of each gas port has an open state permitting the flow of gas through the gas port and a closed state blocking the flow of gas through the gas port;

wherein the at least one chemical or chemical mixture comprises the first chemical composition.

8. A method of testing a device for chemicals comprising:

providing a vapor-sensor bag, a gas source, and the device, wherein the vapor-sensor bag comprises a first and a second gas port;

passing a chemical solution comprising a first chemical composition through the device;

coupling the device to the first gas port;

pumping a first gas composition from the gas source through the device such that the first gas composition mixes with remaining portions of the chemical solution within the device to create a first gas mixture, wherein the first gas mixture inside the device flows into the vapor-sensor bag through the first gas port and exits the vapor-sensor bag through the second gas port;

generating at least one chemical detection output;

if the at least one chemical detection output indicates an unsafe amount of the first chemical composition within the device, repeating the pumping and generating steps;

if the at least one chemical detection output indicates a safe amount of the first chemical composition within the device, stopping the pumping of gas.

9. The method of claim 8, wherein the vapor-sensor bag comprises:

a sealing compartment;

a sensor array integrated with the sealing compartment such that a first side of the sensor array faces an interior of the sealing compartment and a second side of the sensor array faces an exterior of the sealing compartment, wherein the sensor array comprises at least one sensor, wherein each sensor of the at least one sensor is configured to detect at least one chemical or chemical mixture; and at least two gas ports, wherein each gas port comprises a valve, wherein each valve of each gas port has an open state permitting the flow of gas through the gas port and a closed state blocking the flow of gas through the gas port;

wherein the at least one chemical or chemical mixture comprises the first chemical composition.

\* \* \* \* \*